US007821647B2

(12) United States Patent
LeBlanc et al.

(10) Patent No.: US 7,821,647 B2
(45) Date of Patent: Oct. 26, 2010

(54) APPARATUS AND METHOD FOR MEASURING SURFACE TOPOGRAPHY OF AN OBJECT

(75) Inventors: Philip Robert LeBlanc, Corning, NY (US); Vitor Marino Schneider, Painted Post, NY (US); James Patrick Trice, Corning, NY (US)

(73) Assignee: Corning Incorporated, Corning, NY (US)

( * ) Notice: Subject to any disclaimer, the term of this patent is extended or adjusted under 35 U.S.C. 154(b) by 337 days.

(21) Appl. No.: 12/070,844

(22) Filed: Feb. 21, 2008

(65) Prior Publication Data
US 2009/0213386 A1 Aug. 27, 2009

(51) Int. Cl.
G01B 11/02 (2006.01)
(52) U.S. Cl. ...................................... 356/511
(58) Field of Classification Search ................ 356/489, 356/495, 511, 512
See application file for complete search history.

(56) References Cited

U.S. PATENT DOCUMENTS

| 3,338,696 A | 8/1967 | Dockerty |
| 3,682,609 A | 8/1972 | Dockerty |
| 4,575,248 A | 3/1986 | Horwitz et al. ............. 356/353 |
| 4,624,569 A | 11/1986 | Kwon ......................... 356/354 |
| 5,589,938 A | 12/1996 | Deck .......................... 356/359 |
| 5,663,793 A | 9/1997 | De Groot .................... 356/351 |
| 5,710,631 A * | 1/1998 | Bou-Ghannam et al. .... 356/495 |
| 5,777,741 A | 7/1998 | Deck ........................... 356/359 |
| 5,883,717 A | 3/1999 | DiMarzio et al. ........... 356/351 |
| 5,926,266 A * | 7/1999 | Dorundo et al. .......... 356/237.2 |
| 6,304,330 B1 | 10/2001 | Millerd et al. .............. 356/521 |
| 6,522,777 B1 | 2/2003 | Paulsen et al. .............. 382/154 |
| 6,552,808 B2 | 4/2003 | Millerd et al. .............. 356/521 |
| 2005/0260761 A1 | 11/2005 | Lanier et al. .................. 436/55 |
| 2008/0043224 A1 | 2/2008 | Castonguay et al. .......... 356/73 |

FOREIGN PATENT DOCUMENTS

| JP | 2007/225341 | 6/2007 |
| WO | WO2006/000809 | 1/2006 |
| WO | WO2006/080923 | 8/2006 |

OTHER PUBLICATIONS

Sasaki, Kenji, et al. *Optical Aspheric Surface Profiler Using Phase Shift Interferometry*, SPIE Optical Testing and Metrology III, vol. 1332, (Jan. 1, 1991), pp. 97-106.
Hettwer, Andrea, et al., *Three Channel Phase-Shifting Interferometer Using Polarization-Optics and a Diffraction Grating*, Optical Engineering, vol. 39, No. 4, (Apr. 2000), pp. 960-966.
Sivakumar, N.R., et al. *Measurement of Surface Profile in Vibrating Environment with Instantaneous Phase Shifting Interferometry*, vol. 257, No. 2, (Jan. 15, 2006), pp. 217-224.
Cheng and Wyant, *Appl. Opt*, 24, p. 3049 (1985).

* cited by examiner

*Primary Examiner*—Patrick J Connolly

(57) ABSTRACT

An apparatus for measuring surface topography of an object includes an optical arrangement capable of directing a first light beam at a surface of the object, providing a second light beam coherent with and spatially phase-shifted relative to the first light beam, and generating an interference beam from the second light beam and a reflection of the first light beam from the surface of the object. The apparatus further includes at least one line scan sensor for detecting and measuring the interference beam.

12 Claims, 6 Drawing Sheets

APPARATUS AND METHOD FOR MEASURING SURFACE TOPOGRAPHY OF AN OBJECT

FIELD

The invention relates generally to techniques for measuring surface topography of objects. More specifically, the invention relates to a phase measurement interferometry method and apparatus for measuring surface topography of an object.

BACKGROUND

Substrates used in making devices such as flat panel displays, active electronic devices, photovoltaic devices, and biological arrays are typically required to have surfaces that are substantially free of defects and with flatness to within a few microns. Therefore, it is important that these surfaces can be inspected for defects and flatness relatively easily. Phase measurement interferometry (PMI) is an example of an optical interferometry technique for measuring surface topography. PMI generally involves creating interference patterns through interaction of light beams with the surface of an object and detecting the interference patterns, where the detected interference patterns are used to reconstruct the surface topography. PMI generally relies on area scan cameras to detect interference patterns. However, area-based PMI has limited use in high-speed inspection of large substrates, such as those used in flat panel displays. One challenge is that area scan cameras have a limited field-of-view. Another challenge is that area scan cameras are difficult to scale. In general, the larger the area scan camera, the more complex the area scan camera, resulting in long scanning time and high cost.

SUMMARY

In one aspect, the invention relates to an apparatus for measuring surface topography of an object. The apparatus comprises an optical arrangement capable of (i) directing a first light beam at a surface of the object, (ii) providing a second light beam coherent with and spatially phase-shifted relative to the first light beam, and (iii) generating an interference beam from the second light beam and a reflection of the first light beam from the surface of the object. The apparatus further includes at least one line scan sensor for detecting and measuring the interference beam.

In another aspect, the invention relates to a method of measuring surface topography of an object which comprises directing a first light beam at a surface of the object, providing a second light beam coherent with and spatially phase-shifted relative to the first light beam, producing an interference beam from the second light beam and a reflection of the first light beam from the surface of the object, and detecting and measuring the interference beam using at least one line scan sensor.

In yet another aspect, the invention relates to a method of measuring surface topography of an object which comprises directing a first light beam at the surface of the object, providing a second light beam coherent with and spatially phase-shifted relative to the first light beam, producing an interference beam from the second light beam and a reflection of the first light beam from the surface of the object, making multiple copies of the interference beam, passing each copy of the interference beam through one of a plurality of spatial phase splitters, and detecting and measuring the copies of the interference beam using a plurality of line scan sensors associated with the plurality of spatial phase splitters.

Other features and advantages of the invention will be apparent from the following description and the appended claims.

BRIEF DESCRIPTION OF DRAWINGS

The accompanying drawings, described below, illustrate typical embodiments of the invention and are not to be considered limiting of the scope of the invention, for the invention may admit to other equally effective embodiments. The figures are not necessarily to scale, and certain features and certain views of the figures may be shown exaggerated in scale or in schematic in the interest of clarity and conciseness.

DESCRIPTION OF EMBODIMENTS

Figure 1:
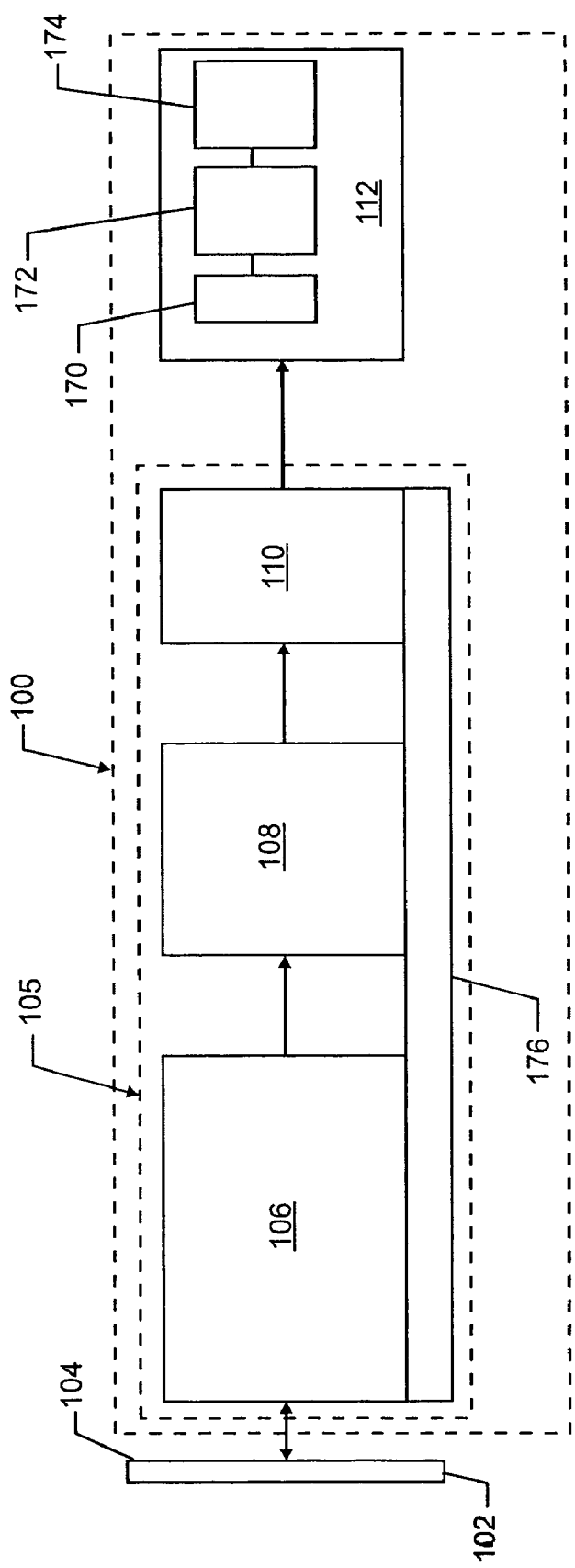
FIG. 1 is a block diagram of an apparatus for measuring surface topography of an object.

The invention will now be described in detail with reference to a few preferred embodiments, as illustrated in the accompanying drawings. In describing the preferred embodiments, numerous specific details are set forth in order to provide a thorough understanding of the invention. However, it will be apparent to one skilled in the art that the invention may be practiced without some or all of these specific details. In other instances, well-known features and/or process steps have not been described in detail so as not to unnecessarily obscure the invention. In addition, like or identical reference numerals are used to identify common or similar elements.

FIG. 1 is a block diagram of an apparatus 100 for measuring surface topography of a test object 102. Apparatus 100 includes an interferometer 105 which measures interference beam patterns generated through optical interaction with a test surface 104 of the test object 102. The interferometer 105 directs a light beam at the test surface 104. The beam size is typically much smaller than the surface area of the test surface 104. The interferometer 105 may be mounted on a translation stage 176 and translated across the test surface 104 for the purposes of obtaining a series of measured interferometer beam patterns from which a surface topography of the test surface 104 can be reconstructed. Alternatively, the test surface 104 may be translated relative to the interferometer 105 for the purposes of obtaining the series of measured interferometer beam patterns. In this case, the test object 102 would be coupled to a translation stage (not shown) to enable such relative motion between the test surface 104 and the interferometer 105. The test surface 104 being interrogated by the interferometer 105 may be small or large in surface area. The test surface 104 may be flat and may or may not include surface defects. Interferometer 105 detects defects in the test surface 104 by measuring surface height variations between the test surface 104 and a reference surface (not shown in FIG. 1). The test object 102 having the test surface 104 may be a substrate for use in devices requiring substrates with high flatness and minimal surface defects, such as flat panel displays, active electronic devices, photovoltaic devices, biological arrays, and sensor arrays. Substrates for making devices such as flat panel displays may be very large, for example, 3 m×3 m. The test object 102 having the test surface 104 may be made of any material suitable for the intended application, such as glass, glass-ceramic, and plastic materials.

Interferometer 105 includes an interference beam generator 106, a beam conditioning module 108, and an imaging module 110. The interference beam generator 106 contains an optical arrangement which directs a first light beam at the test surface 104 and produces an interference beam from a reflection of the first light beam and a second light beam, where the second light beam is coherent with and spatially phase-shifted relative to the first light beam. The coherence referred to herein and in subsequent paragraphs is temporal coherence. The phase shift of the second light beam varies according to the topography of the test surface 104. The beam conditioning module 108 directs the interference beam produced by the optical arrangement in the interference beam generator 106 to the imaging module 110. The beam conditioning module 108 may include any combination of optics, such as collimating lenses, apertures, and diffractive elements, for shaping the interference beam and focusing the interference beam onto the imaging module 110. The imaging module 110 detects and measures the interference beam produced by the interference beam generator 106. Apparatus 100 includes a data acquisition module 112 for collecting the measured data from the imaging module 110. The data acquisition module 112 may include an input/output interface 170 for communication with the imaging module 110, a data recorder 172 for recording the measured data, and a data processor 174 for processing the recorded data. The data processor 174 may execute a process which reconstructs the surface topography of the test surface 104 from the measured data.

Interferometer 105 may be of a Twyman-Green type, a Fizeau type, or other interferometry type suitable for phase measurement interferometry (PMI). However, in contrast to known PMI-based interferometers for measuring surface topography, interferometer 105 uses a system of linear optics. Interferometer 105 uses an imaging module 110 based on line scan sensor(s) to detect and measure multiple interferograms simultaneously from a single interference beam. For high-resolution measurements, the modules in interferometer 105 are designed such that the interference beams detected by the imaging module 110 have a profile that is substantially linear.

Figure 2:
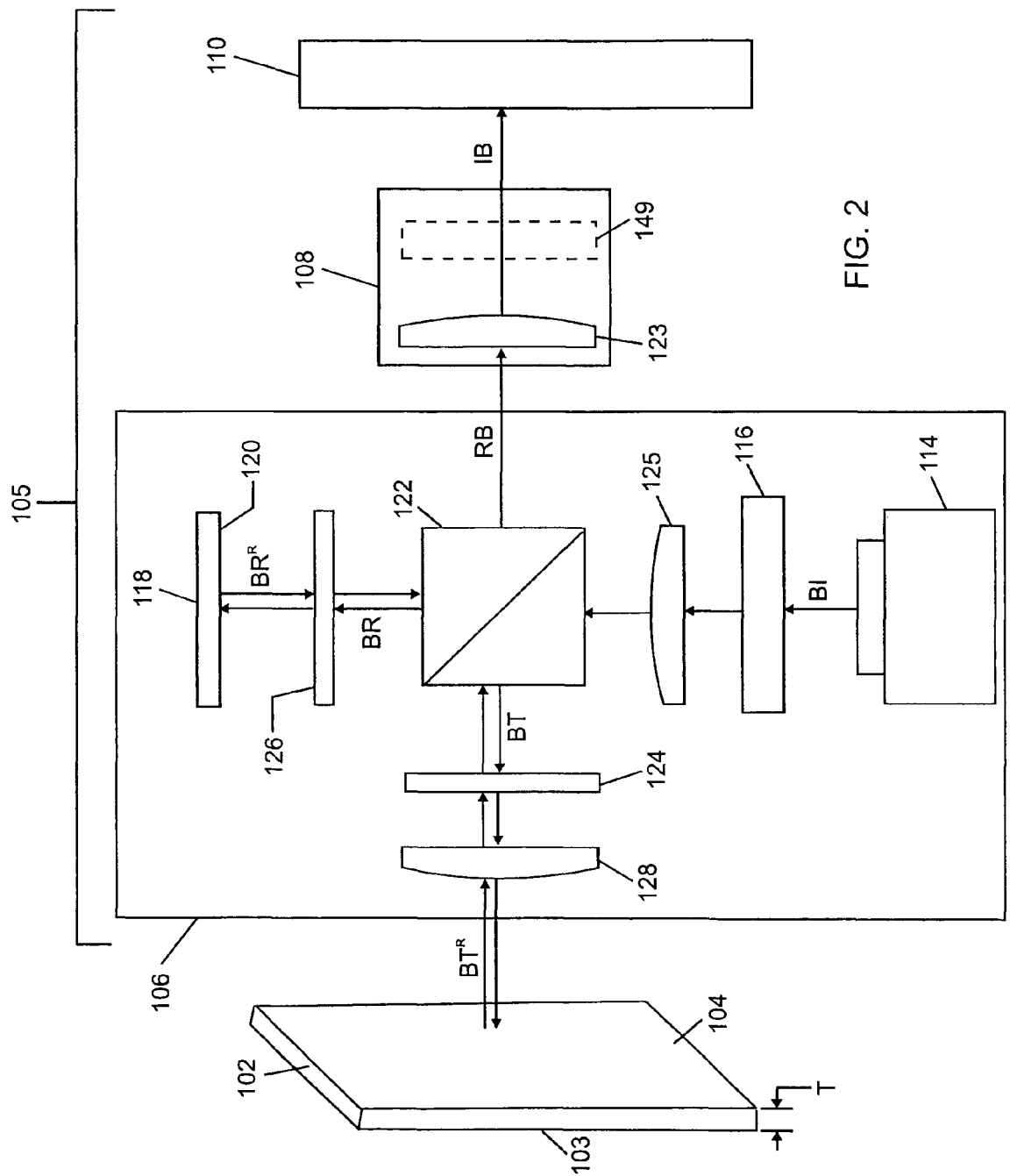
FIG. 2 is a schematic of a Twyman-Green-type interferometer for measuring surface topography of an object.

FIG. 2 shows interferometer 105 in a Twyman-Green configuration. In FIG. 2, interference module 106 includes light source 114 which provides a light beam BI used in interrogating the test surface 104. The light beam BI may be provided using active and/or passive components (not shown separately), which may be local or remote to the light source 114. Where the active components are remote to the light source 114, passive components such as lenses, mirrors, and optical fibers may be used to route the light beam from the remote location where it is generated to the light source 114. The light beam BI provided by the light source 114 may be a low coherence laser beam or other low coherence light beam. In some embodiments, the optical arrangement of the interference beam generator 106 includes a beam shaper 116 for shaping the light beam BI into a desired shape. For enhanced performance with the linear imaging module 110, the beam shaper 116 is preferably a line generator which shapes a nonlinear light beam, e.g., circular beam, into a substantially linear beam, e.g., line beam, highly-elliptical beam, or other high-aspect ratio beam. The beam shaper 116 may be, for example, a diffractive element or a holographic diffuser.

The optical arrangement of the interference beam generator 106 further includes a polarization beam splitter 122 and may further include lens 125. In interference beam generator 106, light beam BI passes through the beam shaper 116 and is focused onto the polarization beam splitter 122 by the lens 125. The polarization beam splitter 122 splits light beam BI into two orthogonally polarized beams BT and BR. In general, light beam BR is coherent with and spatially phase-shifted or phase-separated relative to light beam BT. The optical arrangement of the interference beam generator 106 includes a reference object 118 having a reference surface 120, which is flat and has a known surface topography. Typically, the reference object 118 is a front-surface mirror, or the reference surface 120 may be a surface made of or coated with a reflective material. The light beams BT and BR produced by the polarization beam splitter 122 are directed at the test surface 104 and reference surface 120, respectively. The light beams BT and BR strike the test surface 104 and reference surface 120, respectively, and are reflected back to the polarization beam splitter 122 as reflected light beams $BT^R$ and $BR^R$, respectively. The path lengths of the reflected light beams $BT^R$ and $BR^R$ are influenced by the topography of the test surface 104 and reference surface 120, respectively.

For a low coherence system, the polarization beam splitter 122 is positioned relative to the test surface 104 and reference surface 120 such that the optical length between the polarization beam splitter 122 and each of the test surface 104 and reference surface 120 is within the optical coherence length of the light source 114. Coherence length is the optical distance two light beams can travel before their phase relationship becomes random (and thus no interference pattern will be generated). When light beam BT is incident upon the test surface 104, part of light beam BT is reflected back into the interferometer 105 as reflected light beam $BT^R$. Reflected light beam $BT^R$ recombines with the reflected light beam $BR^R$ from the reference surface 102 and produces an interference beam IB which is detected at the imaging module 110. If the coherence length of the light source 114 is larger than twice the optical thickness of the test object 102, then the portion of the light beam BT which passes through test surface 104 and onto the back surface 103 of the test object 102 will also reflect back into the interferometer 105 and recombine with the reflected light beams $BT^R$ and $BR^R$, contributing to the interference beam IB. In order to minimize or prevent contribution of the back surface reflection to the interference pattern, a light source 114 with a low coherence length is desired. In general, and preferably, the coherence length of the light source 114 is less than the optical thickness of the test object 104. In general and more preferably, the coherence length of the light source 114 is less than twice the optical thickness of the test object 104. Optical thickness of the test object 102 is the product of the thickness (T) of the test object 102, measured along the incidence direction of light beam BT (also known as measurement arm of interferometer 105), and the refractive index of the test object 102.

Quarter-wave plates 124, 126 are disposed in the optical paths between the polarization beam splitter 122 and the test and reference surfaces 104, 120, respectively. The quarter-wave plates 124, 126 change linearly polarized light to circularly polarized light and vice versa. In the forward direction, the quarter-wave plates 124, 126 function such that light beams BT and BR which are linearly polarized at the polarization beam splitter 122 are circularly polarized at the test and reference surfaces 104, 120. In the reverse direction, the quarter-wave plates 124, 126 function such that the reflected light beams $BT^R$ and $BR^R$ which are circularly polarized at the test and reference surfaces 104, 120 are linearly polarized at the polarization beam splitter 122. In some embodiments, a focusing lens 128 is used to focus the light beam BT from polarization beam splitter 122 or quarter-wave plate 124 onto the test surface 104. A focusing lens (not shown) may be similarly used to focus beam BR from polarization beam splitter 122 or quarter-wave plate 126 onto the reference surface 120.

The reflected light beams $BT^R$ and $BR^R$ received at the polarization beam splitter 122 form recombined beam RB upon exiting the polarization beam splitter 122. Recombined beam RB is received in the beam conditioning module 108 and exits the beam conditioning module 108 as interference beam IB. Imaging module 110 detects and measures interference beam IB is detected and measured. As previously mentioned, the beam conditioning module 108 includes optics for conditioning and focusing beams onto the imaging module 110. In the example shown in FIG. 2, the beam conditioning module 108 includes a focusing lens 123 for focusing the recombined beam RB onto the imaging module 110. The beam conditioning module 108 may optionally include optics module 149 for optionally making copies of the recombined beam and providing the copies of the recombined beam to the imaging module 110. Optics module 149 may include, for example, a diffractive element or a holographic diffuser. Optics module 149 is useful when the imaging module 110 includes a plurality of line scan sensors for measuring interference beams, as will be described in detail later.

Figure 3:
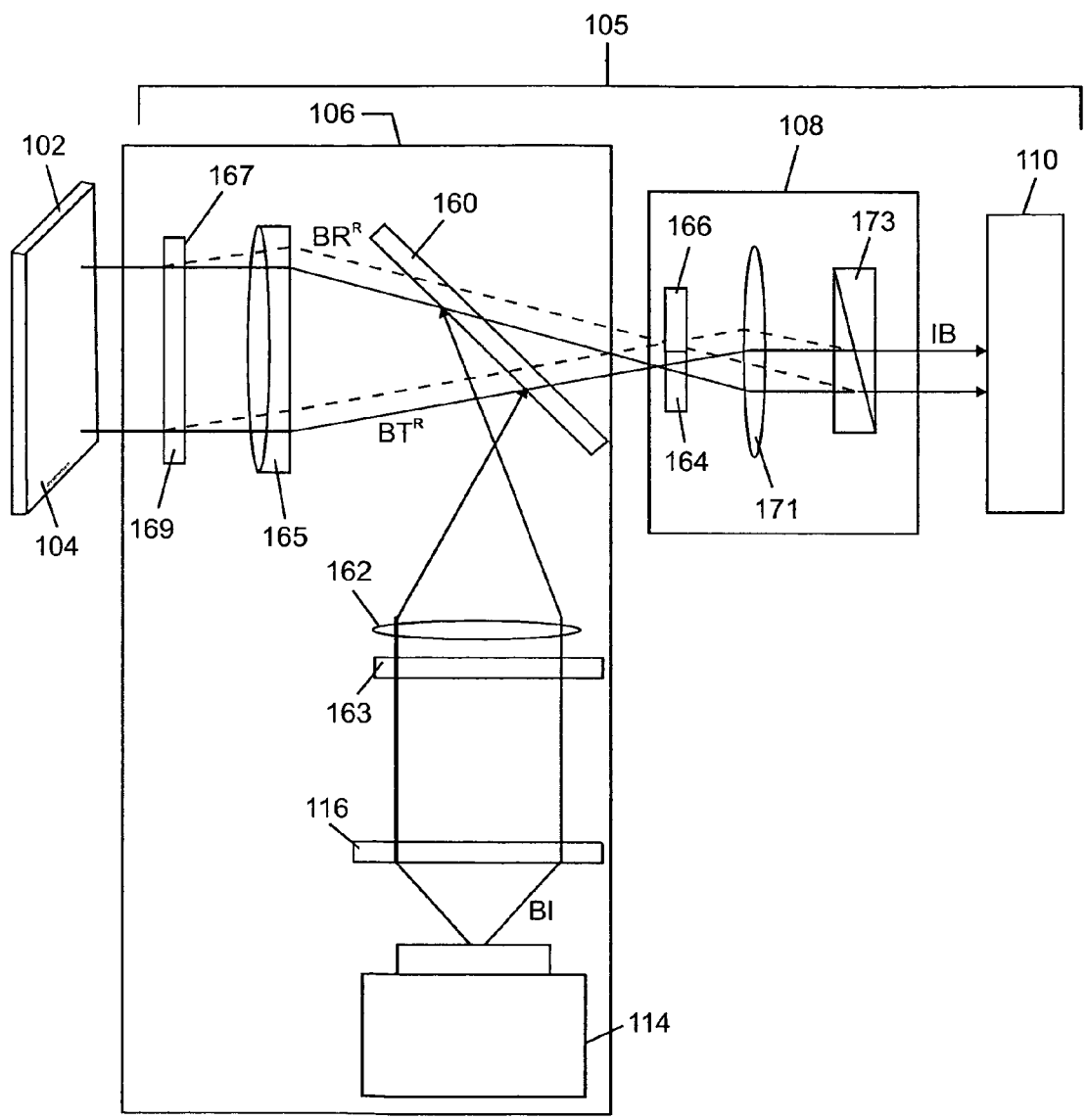
FIG. 3 is a schematic of a Fizeau-type interferometer for measuring surface topography of an object.

FIG. 3 shows interferometer 105 in a Fizeau configuration, such as described in International Publication WO 2006/080923. In FIG. 3, interference beam generator 106 includes light source 114, as described above, which provides a light beam BI used in interrogating the test surface 104 of test object 102. The light beam BI provided by light source 114 passes through beam shaper 116, as described above, half-wave plate 163, and beam expansion lens 162, and is then incident on beam splitter 160. Light beam BI upon striking the beam splitter 160 is reflected towards the test surface 104 of the test object 102 and a reference surface 167 of a reference object 169. Light beam BI from beam splitter 160 may be focused onto surfaces 104, 167 by collimation lens 165. In the configuration shown in FIG. 3, the test surface 104 and reference surface 167 are inline and tilted relative to each other so that beams $BT^R$ and $BR^R$ reflected from these surfaces are spatially separate. As in the previous example, light beams $BT^R$ and $BR^R$ are also coherent. In general, and preferably, the coherence length of the light source 114 is less than the sum of the optical thickness of the test object 104 and the reference object 169. In general, and more preferably, the coherence length of the light source 114 is less than twice the sum of the optical thickness of the test object 104 and the reference object 169. Optical thickness of the test object 102 has been defined above. Optical thickness of the reference object 169 is the product of the thickness of the reference object 169 (measured along the measurement arm of interferometer 105) and the refractive index of the reference object 169. In the configuration shown in FIG. 3, the reference object 169 is made of a transparent material. The reference object 169 could be a transparent lens with a flat reference surface 167, for example. The reflected beams $BT^R$ and $BR^R$ pass through the beam splitter 160 and are received in the beam conditioning module 108. In the beam conditioning module 108, the reflected light beams $BT^R$ and $BR^R$ converge at a point in the focal plane of a collimation lens 164. A spatial polarization filter 166 is arranged at the focal plane of the collimation lens 164 such that the reflected light beams upon leaving the collimation lens 164 have orthogonal polarization states. The light beams having orthogonal polarization states may additionally pass through an imaging lens 171 and a polarization beam splitter 173 and exit the beam conditioning module as interference beam IB. The imaging module 110 detects and measures the interference beam IB.

Figure 4:
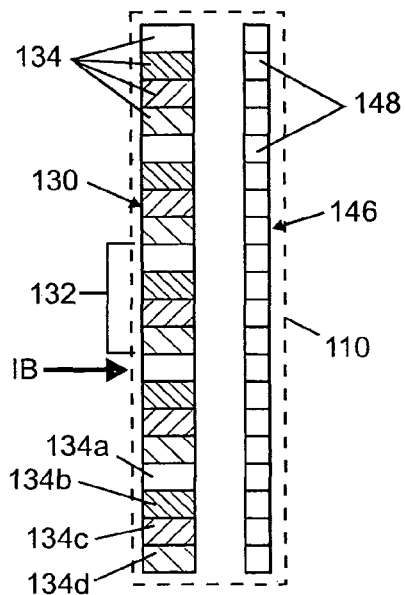
FIG. 4 is a schematic of an imaging module including a linear pixelated phase mask and a line scan sensor.

Referring to FIGS. 1-3, imaging module 110 is arranged downstream of the beam conditioning module 108. In some embodiments, as illustrated in FIG. 4, imaging module 110 includes a linear pixelated phase mask 130 as a spatial phase splitter. In some embodiments, the linear pixelated phase mask 130 is a linear array of polarization elements 134 in a repeating pattern. In some embodiments, the arrangement of the polarization elements 134 in the linear array is such that no two neighboring polarization elements 134 have the same polarization angles. Herein, polarization angles are relative to the detection axis or reference arm of the interferometer (105 in FIGS. 1-3). Each repeating unit 132 includes polarization elements 134 having different polarization angles. In some embodiments, each repeating unit includes four polarization elements 134, each having a polarization angle selected from 0°, 90°, 180°, and 270°. In some embodiments, the polarization elements 134 within each repeating unit are arranged such that the difference in polarization angle between neighboring polarization elements 134 is 90°. As an example, a repeating unit 132 may include a sequential arrangement of polarization element 134a having polarization angle 0°, polarization element 134b having polarization angle 90°, polarization element 134c having polarization angle 180°, and polarization element 134d having polarization angle 270°.

Figure 5:
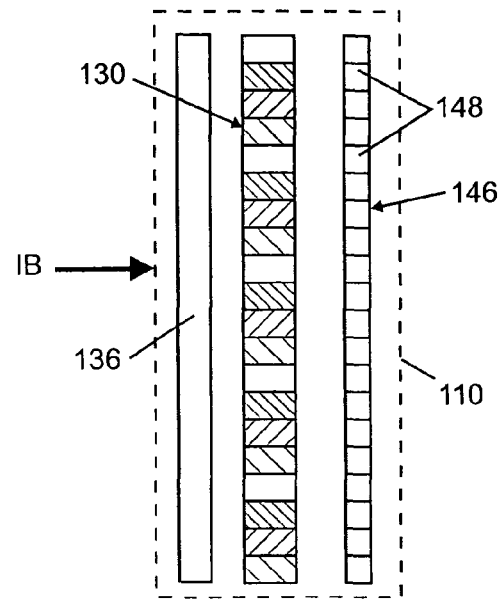
FIG. 5 is a schematic of the imaging module of FIG. 4 with a quarter-wave plate preceding the linear pixelated phase mask.

FIG. 5 shows the imaging module 110 of FIG. 4 with a quarter-wave plate 136 preceding the linear pixelated phase mask 130. The quarter-wave plate 136 converts a circularly polarized input beam into a linearly polarized input beam and vice versa and is useful when the input beam IB into the imaging module 110 is not circularly polarized or is linearly polarized. In FIGS. 4 and 5, the linear pixelated phase mask 130 interrogates intensity of the input beam at different phase delays or phase shifts. The number of phase shifts corresponds to the number of different polarization states represented within the linear pixelated phase mask 130. For example, where the linear pixelated phase mask 130 has a repeating unit of polarization elements and each repeating unit includes four different polarization angles, the number of phase delays interrogated in the input beam would be four. This would allow the imaging module 110 to detect and measure four interferograms simultaneously.

In FIGS. 4 and 5, the imaging module 110 further includes a line scan sensor 146 associated with the pixelated phase mask 130 for detecting and measuring interferograms passing through the pixelated phase mask 130. The line scan sensor 146 includes a linear array of photo elements 148. In the particular arrangements shown in FIGS. 4 and 5, there is a one-to-one mapping between the photo elements 148 of the line scan sensor 146 and the polarization elements 148 of the linear pixelated phase mask 130. The line scan sensor 146 detects and measures the intensity of the interference beam passing through the linear pixelated phase mask 130 at the different polarization states and phase delays represented in the linear pixelated phase mask 130.

Figure 6:
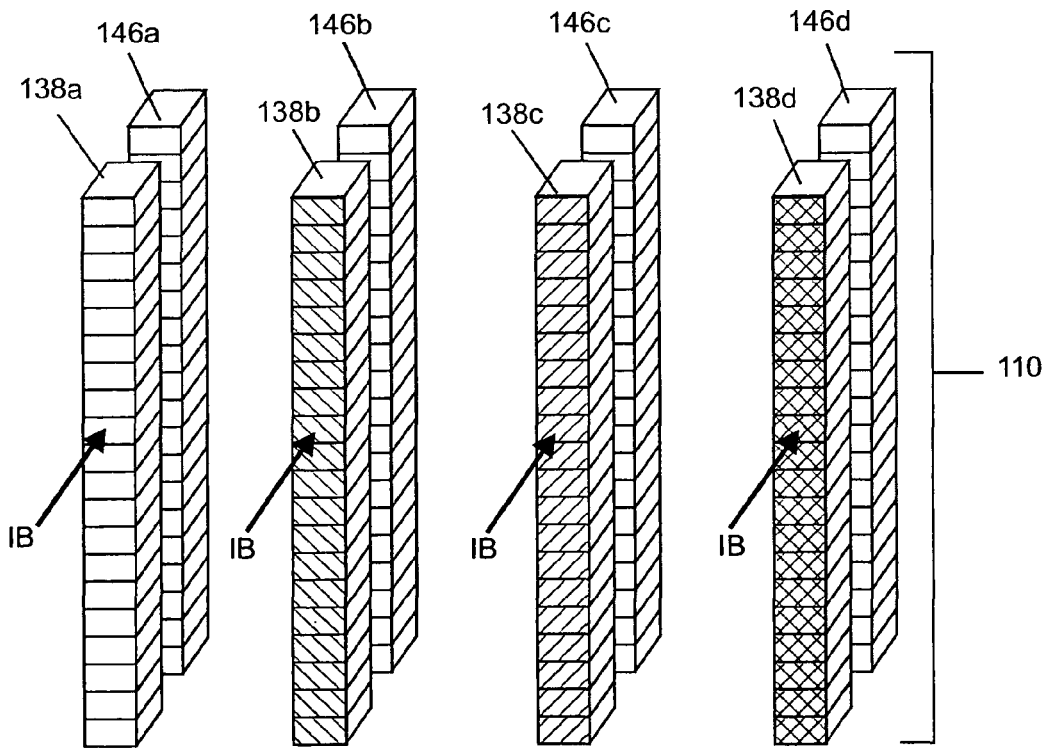
FIG. 6 is a schematic of an imaging module including a plurality of pixelated phase masks and line scan sensors.

FIG. 6 depicts an example where the imaging module 110 includes linear polarization arrays 138a, 138b, 138c, 138d. In general, the imaging module 110 may have two more linear polarization arrays, with at least three linear polarization arrays being generally preferred. Each of the linear polarization arrays 138a, 138b, 138c, 138d includes a set of polarization elements. In one example, the linear polarization array 138a includes polarization elements having a first polarization angle, the linear polarization array 138b includes polarization elements having a second polarization angle, the linear polarization array 138c includes polarization elements having a third polarization angle, and the linear polarization array 138d includes polarization elements having a fourth polarization angle, where the first, second, third, and fourth polarization angles are different. As an example, the first, second, third, and fourth polarization angles are selected from 0°, 90°, 180°, and 270°. In this arrangement, each of the linear polarization arrays 138a, 138b, 138c, 138d interrogates the intensity of the input beam at different phase delays or phase shifts. As in FIG. 5, each of the linear polarized array 138a, 138b, 138c, 138d may be preceded by a quarter-wave plate if the input beam is linearly polarized. The polarization arrays 138a, 138b, 138c, 138d work similarly to the linear pixelated phase mask (130 in FIGS. 4 and 5), except that each polarization array is dedicated to a single polarization state. Four copies of the input or interference beam IB are required for the four polarization arrays 138a, 138b, 138c, 138d. The four copies of the input beam IB can be provided by optics module (149 in FIG. 2), such as diffractive element or holographic diffuser, in the beam conditioning module (108 in FIG. 2). The optics module providing the four copies of the input beam IB could also be positioned at the input end of the imaging module 110, rather than in the beam conditioning module.

In FIG. 6, the imaging module 110 includes line scan sensors 146a, 146b, 146c, 146d associated with the linear polarization arrays 138a, 138b, 138c, 138d, respectively. The line scan sensors 146a, 146b, 146c, and 146d are similar to the line scan sensor 146 described in FIGS. 4 and 5 and detect interferograms passing through the linear polarization arrays 138a, 138b, 138c, 138d, respectively.

Figure 7:
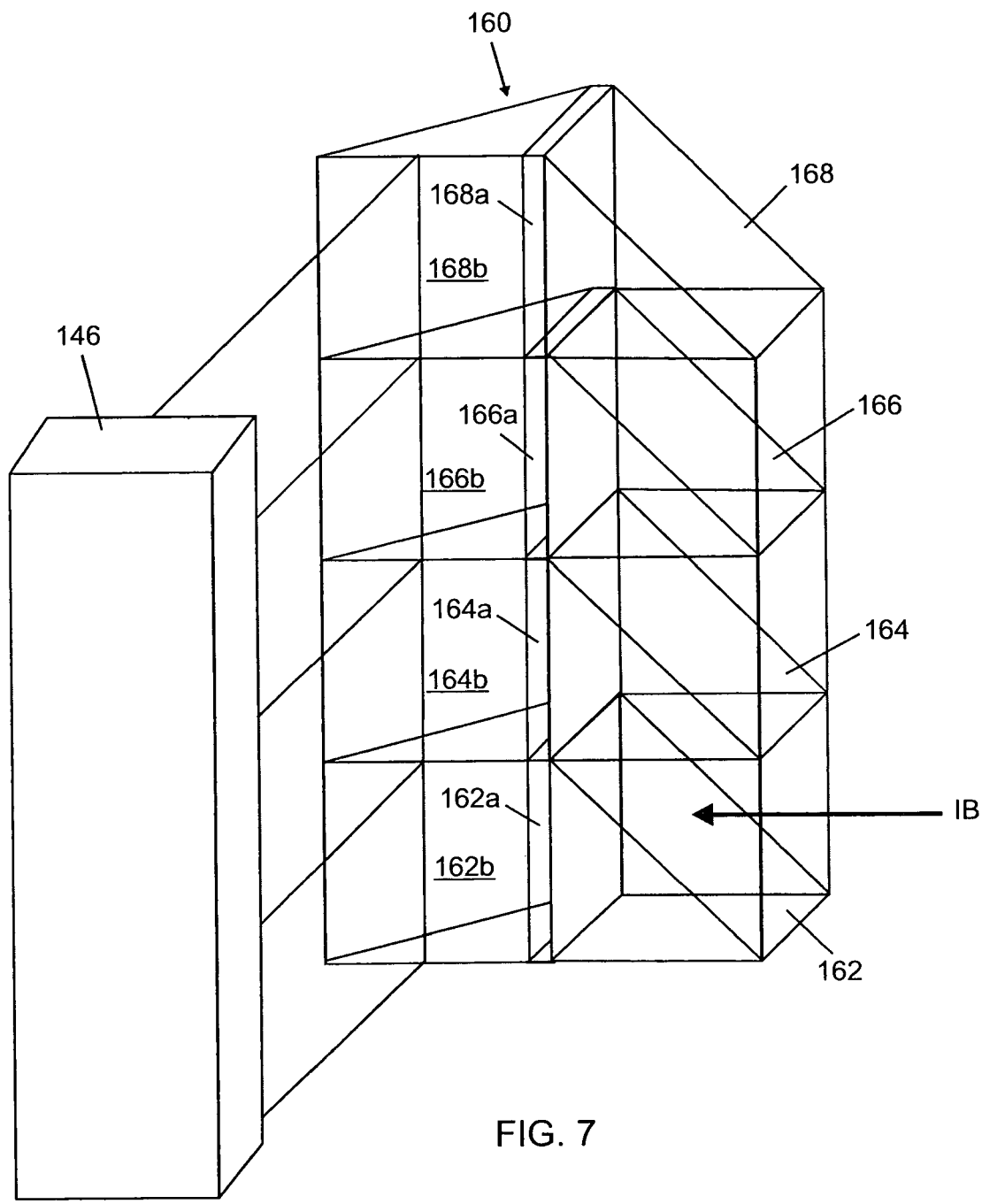
FIG. 7 is a perspective view of a linear prismatic phase shifter optically coupled to a line scan sensor.
Figure 8:
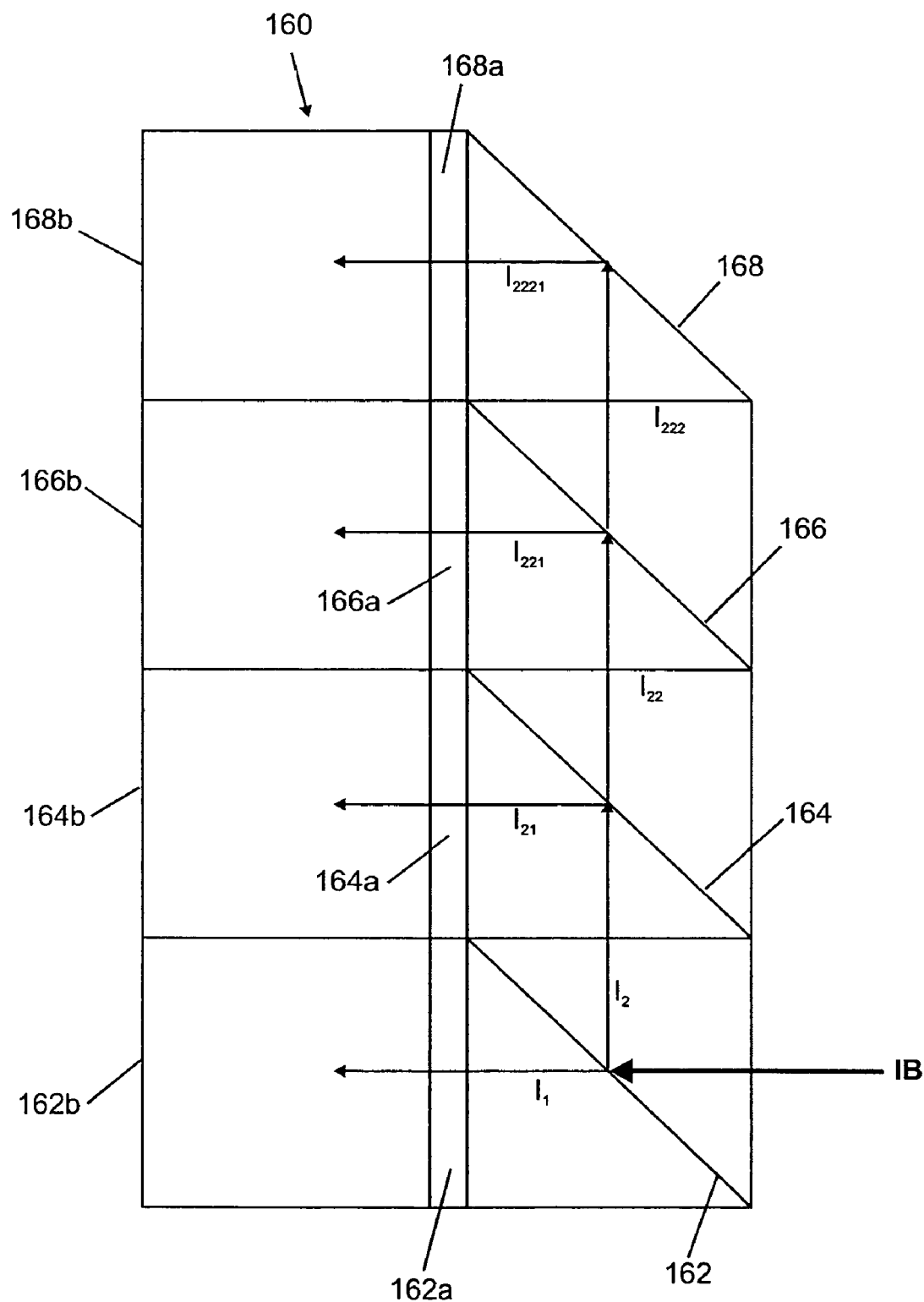
FIG. 8 is a front view of the linear prismatic phase shifter of FIG. 7.

FIGS. 7 and 8 show a linear prismatic phase shifter 160 that could be used as a spatial phase splitter and in place of the linear pixelated phase mask (130 in FIGS. 4-5 and 138a-d in FIG. 6). The linear prismatic phase shifter 160 includes beam splitter 162, polarization beam splitter 164, beam splitter 166, and prism or mirror 168 arranged in a linear stack. Adjacent to the stack of splitters 160, 162, 164 and prism or mirror 168 are bare plate 162a, quarter-wave plate 164a, bare plate 166a, and quarter-wave plate 168a, respectively, arranged in a linear stack. Adjacent to the stack of plates are triangular prisms 162b, 164b, 166b, and 168b arranged in a linear stack. Referring to FIG. 8, input beam IB is received at beam splitter 162. Beam splitter 162 splits input beam IB into two light beams $I_1$ and $I_2$. Beam $I_1$ passes through the bare plate 162a into the prism 162b. A portion of the line scan sensor (146 in FIG. 7) would be aligned with the prism 162b to receive the output beam from the prism 162b. Light beam $I_2$ travels to polarization beam splitter 164, where it is again split into two light beams $I_{21}$ and $I_{22}$ having orthogonal polarization states. Light beam $I_{21}$ passes through the quarter-wave plate 164a into the prism 164b. A portion of the line scan sensor (146 in FIG. 7) receives the output beam from prism 164b. Light beam $I_{22}$ travels to beam splitter 166, where it is split into two light beams $I_{221}$ and $I_{222}$. Light beam $I_{221}$ passes through the bare plate 166b and prism 166b and is received at the line scan sensor (146 in FIG. 7). Light beam $I_{222}$ travels to prism or mirror 168. A reflected beam $I_{2221}$ of light beam $I_{222}$ passes through quarter-wave plate 168a and prism 168b. A portion of the line scan sensor (146 in FIG. 7) receives the output of prism 168b. The beam splitters and polarization beam splitters 162, 164, 166, 168 are preferably designed such that the output beams are closely matched in intensity and have similar signal-to-noise ratios.

Referring to FIGS. 1-3, the interference beam generator 106 generates an interference beam through optical interaction with the test surface 104 of the test object 102. The interference beam IB passes through the beam conditioning module 108 and is focused onto the imaging module 110. Inside the imaging module 110, the input beam IB is interrogated at different phase delays by the linear pixelated phase mask (130 in FIGS. 4 and 5) or the linear polarization arrays (138a-d in FIG. 6) or the linear prismatic phase shifter (160 in FIGS. 7 and 8), collectively referred to as spatial phase splitter(s), depending on which configuration of the imaging module 110 is used. Inside the imaging module 110, the line scan sensor (146 in FIGS. 4 and 5) or a plurality of line scan sensors (146a-d in FIG. 6) detects and measures the interferograms passing through the linear pixelated phase mask (130 in FIGS. 4 and 5) or the linear polarization arrays (138a-d in FIG. 6) or the linear prismatic phase shifter (160 in FIGS. 7 and 8), collectively referred to as spatial phase splitter(s), depending on which configuration of the imaging module 110 is used. The interferometer 105 is translated linearly across the test surface 164 while the interference beam generator 106 generates an interference beam at each position of the interferometer 105 across the test surface 104. Alternatively, the test surface 104 may be translated linearly relative to the interferometer 105 while the interferometer beam generator 106 generates the interference beam. The interference beams generated by interferometer 105 are detected and measured by the imaging module 110 as previously explained. For each interference beam generated by the interference beam generator 106, the imaging module 110 detects and measures a plurality of interferograms from the interference beam simultaneously. The measured data may be transmitted to the data acquisition module (112 in FIG. 1) and processed to reconstruct the surface topography using well known techniques, such as described in Cheng and Wyant, Applied Optics, 24, p. 3049 (1985).

The linearity of interferometer 105 facilitates scalability of the surface topography measurement system. To measure the surface topography of a test surface, the size of the interferometer 105 only needs to match the test surface along one dimension or a first dimension. The full surface topography is acquired by relative motion between the linear interferometer 105 and the test surface along a second dimension substantially orthogonal to the first dimension while the interferometer 105 makes measurements. Linear scaling of the components of the imaging module 110 can be done relatively easily and cheaply because all that is required is addition of elements in a linear direction to the spatial phase splitter (130 in FIGS. 4 and 5; 138a-d in FIG. 6, 160 in FIGS. 7 and 8) and the line scan sensor (146 in FIGS. 4, 5, and 7; 146a-d in FIG. 6). Alternatively, a linear array of interferometers 105 can be used to cover the test surface along a first linear direction, and relative motion between the linear array of interferometers 105 and the test surface along a second linear direction substantially orthogonal to the first linear direction can be used to generate the two-dimensional surface topography. Because of the linearity of the interferometer 105, alignment of the interferometer 105 with the test surface is relatively simple. This facilitates deployment of the interferometer 105 for online measurements in a manufacturing environment.

Apparatus 100 can be used for online measurement of the surface topography of an object. The measured surface topography can be used to detect the presence of defects on the measured surface of the object. In objects such as substrates used in making flat panel displays, these defects may be on the order of a few hundred microns to a few millimeters long and may occur anywhere on the measured surface of the object. The measured surface itself may be very large, for example, 3 m×3 m. With defects less than 1 micron in height, vibrations is of concern. Apparatus 100 uses instantaneous phase measurement interferometry (i-PMI) to substantially eliminate vibration effects on measurements made along a line of the test or measured surface. In i-PMI, multiple interferograms are extracted from a single interference beam. The interference beam itself is produced within a timeframe in which the test surface is practically "frozen." At 5 microsecond interferometer exposure, test surface vibrations greater than 50 micrometer amplitude and faster than 20 Hz frequencies will be practically frozen, allowing surface topography to be measured accurately down to 1 nm or less. In addition, the two-dimensional surface topography can be generated with minimized local vibration effects by moving the interferometer 105 relative to the measured surface at a high scan rate. At a high scan rate, vibration is frozen both for measurement along a line and in a local area. The two-dimensional surface topography would then be a concatenation of local topography measurements, with each local topography measurement captured during a timeframe when the test surface is practically "frozen." Within each local topography measurement, detection of defects would be consistent and reliable. There are various methods for analyzing a large topography map for local defect signatures. One method includes transforming the large topography map into a Fourier map of the spatial frequencies (or temporal frequencies since the scan rate is known) and then applying a high pass filter or band-pass filter in order to isolate the defects.

Apparatus 100 may also be used for measuring surface topography while forming a sheet of material using fusion draw processes, such as described in U.S. Pat. Nos. 3,338,696 and 3,682,609 issued to Dockerty, herein incorporated by reference. In fusion draw processes, the sheet of material may be subject to motions such as vibration while being drawn. High-resolution measurements can be made if the interferometer 105 is swept across the sheet of material at a speed faster than the vibration of the sheet of material.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An apparatus for measuring surface topography of an object, comprising:
    an optical arrangement capable of (i) directing a first light beam at a surface of the object, (ii) providing a second light beam coherent with and spatially phase-shifted relative to the first light beam, and (iii) generating an interference beam from the second light beam and a reflection of the first light beam from the surface of the object;
    at least one line scan sensor for detecting and measuring the interference beam; and
    at least one spatial phase shifter optically coupled to the at least one line scan sensor for interrogating the interference beam at different phase delays, wherein the at least one spatial phase shifter is a linear pixelated phase mask comprising a linear arrangement of polarization elements.

2. The apparatus of claim 1, further comprising a light source capable of providing a source light beam with a coherence length less than twice an optical thickness of the object.

3. The apparatus of claim 2, wherein the optical arrangement includes a beam splitter capable of splitting the source light beam into the first light beam and the second light beam.

4. The apparatus of claim 3, wherein the optical arrangement includes a reference surface which interacts with the second light beam.

5. The apparatus of claim 2, wherein the optical arrangement further comprises a beam shaper capable of shaping the source light beam into a substantially linear beam.

6. The apparatus of claim 1, wherein the polarization elements are arranged in a repeating pattern and the polarization elements in each repeating pattern have different polarization angles.

7. The apparatus of claim 1, which comprises a plurality of independent line scan sensors.

8. The apparatus of claim 7, comprising a plurality of spatial phase shifters optically coupled to the plurality of line scan sensors for interrogating the interference beam at different phase delays.

9. The apparatus of claim 8, further comprising an optical module for making copies of the interference beam such that a copy of the interference beam is received at each spatial phase shifter.

10. The apparatus of claim 1, further comprising a mechanism for moving the optical arrangement and the at least one line scan sensor relative to the surface of the object.

11. The apparatus of claim 1, further comprising a data acquisition module for collecting data from the at least one line scan sensor and processing the data to reconstruct the surface topography.

12. A method of measuring surface topography of an object, comprising:
    directing a first light beam at the surface of the object;
    providing a second light beam coherent with and spatially phase-shifted relative to the first light beam;
    producing an interference beam from the second light beam and a reflection of the first light beam from the surface of the object;
    making multiple copies of the interference beam;
    passing each copy of the interference beam through one of a plurality of spatial phase splitters; and
    detecting and measuring the copies of the interference beam using a plurality of line scan sensors associated with the plurality of spatial phase splitters.

* * * * *